United States Patent [19]

Geat et al.

[11] Patent Number: 4,560,377
[45] Date of Patent: Dec. 24, 1985

[54] ENDERMIC INJECTOR DEVICE

[75] Inventors: Mario Geat, Lucinicco; Luciano Dornik, Gorizia, both of Italy

[73] Assignee: SICIM SpA, Romans d'Isonzo, Italy

[21] Appl. No.: 572,387

[22] Filed: Jan. 20, 1984

[30] Foreign Application Priority Data

Jan. 24, 1983 [IT] Italy .............................. 83310 A/83

[51] Int. Cl.$^4$ ............................................. A61M 5/30
[52] U.S. Cl. ......................................... 604/68; 604/71
[58] Field of Search ....................... 604/68, 69, 70, 71, 604/72

[56] References Cited

U.S. PATENT DOCUMENTS

| 2,754,818 | 7/1956 | Scherer | 604/68 |
| 2,928,390 | 3/1960 | Venditty et al. | 604/70 |
| 3,202,151 | 8/1965 | Kath | 604/71 |
| 3,521,633 | 7/1970 | Yahner | 604/71 |
| 3,763,859 | 10/1973 | Yanof et al. | 604/71 X |
| 4,059,107 | 11/1977 | Iriguchi et al. | 604/71 |

Primary Examiner—John D. Yasko
Attorney, Agent, or Firm—Wegner & Bretschneider

[57] ABSTRACT

This invention concerns an endermic injector device (10) for subcutaneous injections without a needle, said device (10) being suitable for injecting under pressure at least one fluid drawn in a measured dose from replaceable phials (15) which are advantageously of a throwaway kind, whereby nozzle means (18), means to aspirate fluid, means to expel fluid and means to provide the required expulsion force are comprised, said device (10) including in cooperation:

an aspiration and ejection group (27) consisting of valve means (19) to draw and deliver fluid, a cylindrical chamber (33) to hold fluid together with a removable small piston (34), and safety means with an alignment head (32), a group to control aspiration and expulsion (29) which comprises means for axial withdrawal of said small piston (34), tripping means (36–38) and spring means (52) for the axial forward movement of said small piston (34), means to regulate (60) the pre-loading of said spring means (52) and means (30) to display the quantity of the dose, and means (14) to hold and position said phials (15).

14 Claims, 11 Drawing Figures

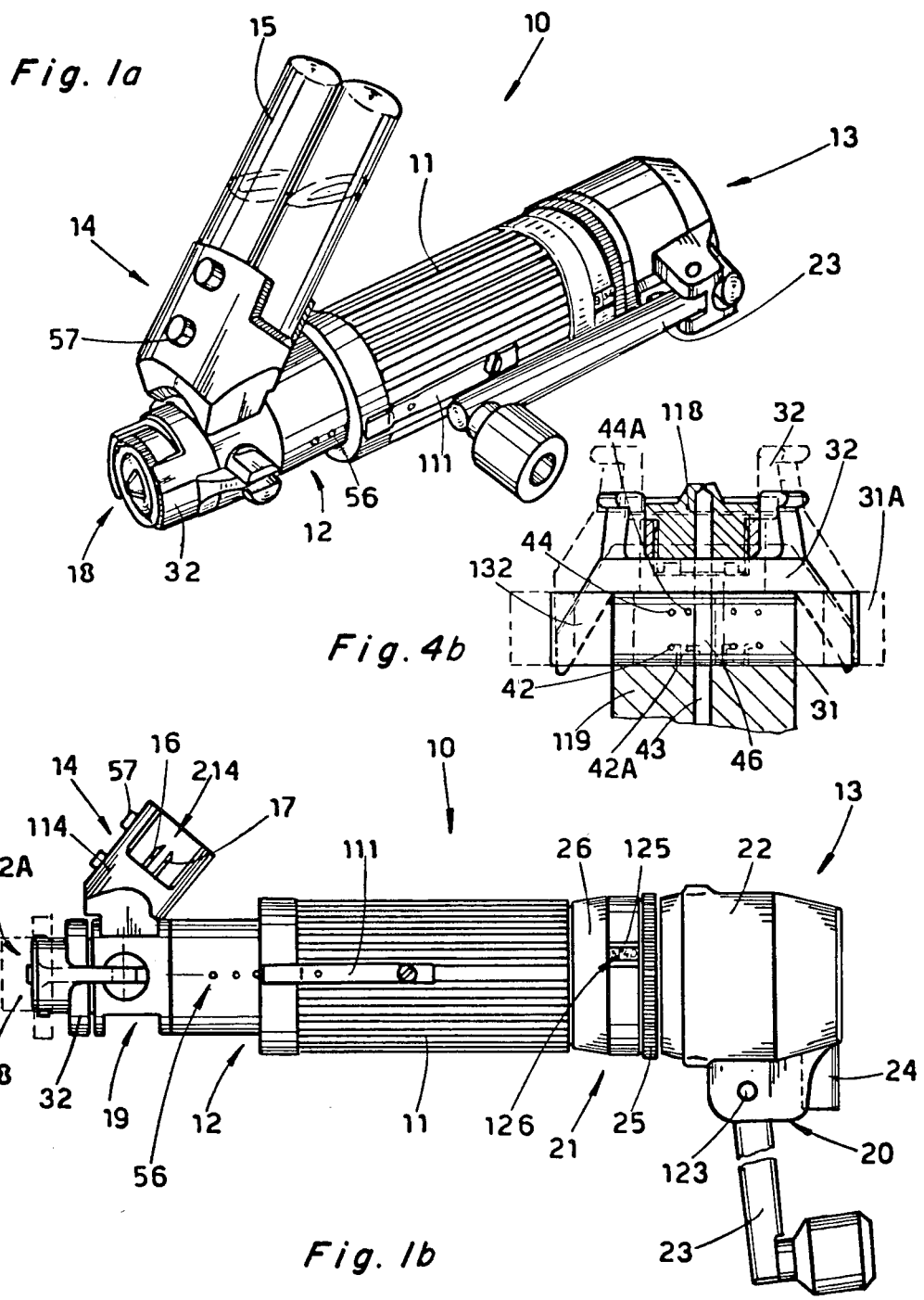

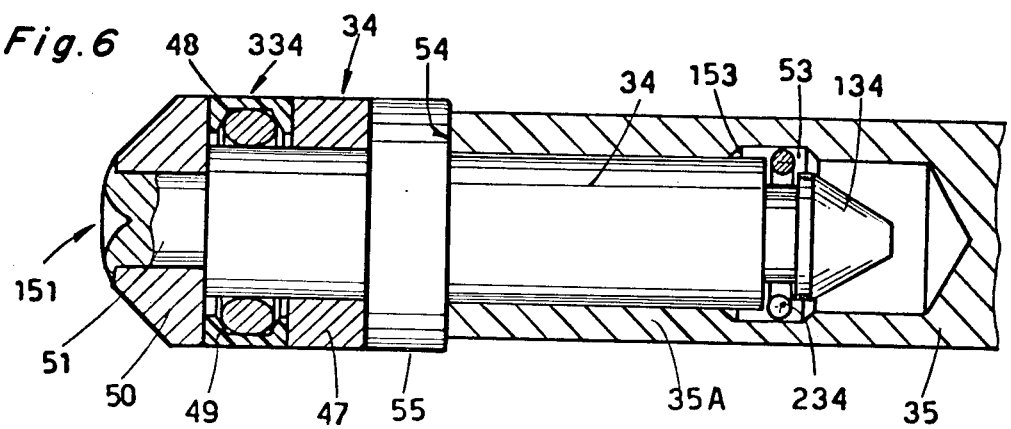
Fig. 6
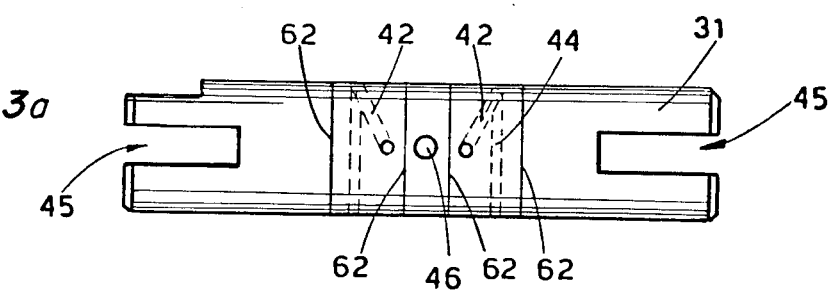
Fig. 3a
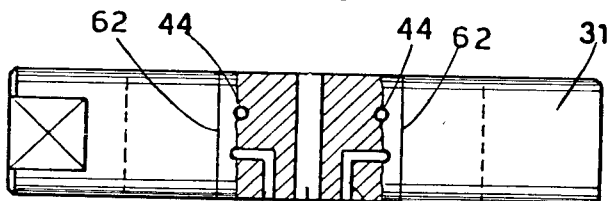
Fig. 3b
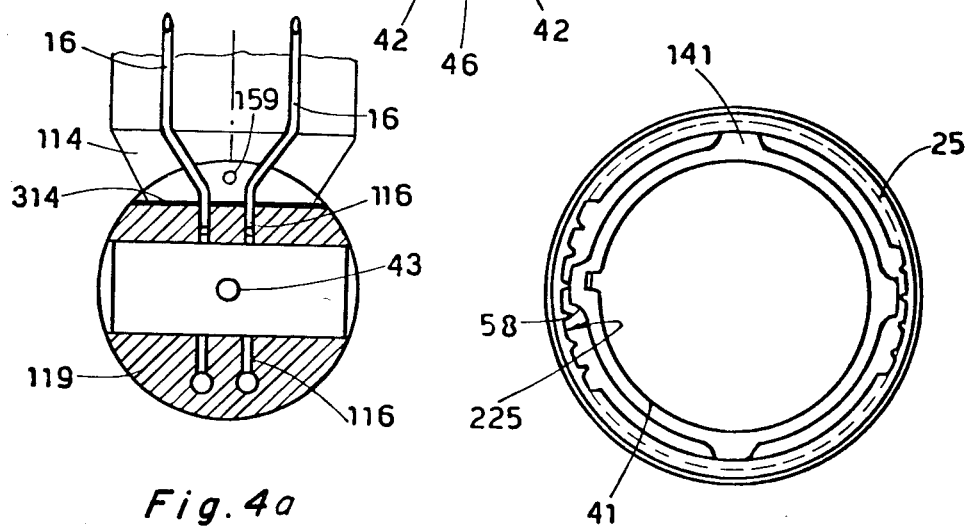
Fig. 4a
Fig. 5

ENDERMIC INJECTOR DEVICE

This invention concerns an endermic injector device. To be more exact, the invention concerns an endermic injector able to carry out intracutaneous injection of liquids without a needle by means of a jet of fluid under high pressure.

The injector of the invention makes it possible to regulate the dose of the liquid to be injected and also makes it possible to regulate the possible dosing and mixture of two or more liquids and is particularly suitable for injections of insulin although it is not restricted thereto.

Indeed, the use of two or more different qualities of insulin for suitable mixing is often required for such injections.

The known art envisages various endermic injection devices, but they all entail many drawbacks.

U.S. Pat. No. 2,717,597 shows an injector apparatus with a very complicated structure. Said injector comprises in the zone of its head a chamber for lodging a special phial containing the medicament.

This apparatus involves considerable difficulties during loading since it cannot be loaded from outside but has to be partly dismantled for insertion of said phial for each injection.

Said apparatus also has an inadequate safety system and is not completely hygienic, besides not allowing the medicament to be drawn from the normal phials commercially available.

Moreover, with this device the dose injected is fixed or else, if it is wished to vary the dose, it is necessary to use phials of differing capacities.

U.S. Pat. No. 2,737,946 too concerns an injector having a very complicated structure. In this case also the medicament is held in a special phial, which is inserted near the head of the injector at the time when it is to be used.

This invention, like the one before it, does not allow the medicament to be loaded from the outside with the normal, commercially available phials nor does it allow every desired dose to be administered.

Furthermore, the pressure which thrusts the medicament through the small outlet hole is generated by a gas which is compressed beforehand during loading and which is held momentarily in a chamber within said apparatus. The high pressures to which the gas has to be compressed entail difficulties in providing a gastight seal and prejudice the working life of the apparatus itself.

U.S. Pat. No. 2,928,390 envisages an injector device which enables the medicament to be loaded and the dose to be regulated from the outside and to be drawn from normal, commercially available phials.

Said device works in two stages, of which the first and speedier stage enables the medicament to overcome the compactness of the skin, whereas the next and slower stage permits excellent penetration by the medicament.

This device has an outstandingly complex structure, which makes it heavy, hard to handle and very costly; moreover, sterilization and maintenance of the device are a great problem.

The loading of the springs which provide the thrust for the cylinders that generate the outlet pressure of the medicament is also carried out with compressed air. This involves a considerable drawback as the injections can only be administered when an independent means to compress air is available.

The device displayed in U.S. Pat. No. 3,330,276 enables the dose to be regulated and the medicament to be loaded from outside and to be drawn from normal, commercially available phials.

This apparatus has a very heavy, complex structure and also comprises a very complicated system for fitting and positioning the phial, thereby entailing overall some considerable handling difficulties.

Moreover, the phial itself is hardly protected at all and is subject to breakage, a fact which restricts the ability to carry the device from place to place by hand or on the person.

Furthermore, with such a device only one type of medicinal can be loaded at a time; this factor limits its use since some patients such as diabetics, for instance, need injections of which the components are drawn from different phials and mixed advantageously before being injected.

In said invention the thrust applied by the elastic means to expel the medicament may not be strong enough, above all because of the complexity and weight of the parts of which the device consists.

Furthermore, the power of the group that propels the medicament cannot be regulated.

Moreover, a noteworthy shortcoming of said device is the presence of an air filter fitted near the container of the phial, this filter being needed to maintain the required pressure within the phial itself during the loading of the medicinal and also to maintain sterile conditions within the phial itself.

Moreover, the invention provides difficulties in dismantling for sterilization and maintenance and needs service keys.

A further drawback lies in the fact that, if the valve is ever left inadvertently in the drawing position, the phial may explode when the apparatus is operated. Besides, after being operated, the device has to be fully unloaded before it can be recharged.

U.S. Pat. No. 3,330,277 proposes a variant of U.S. Pat. No. 3,330,276 but without applying any substantial functional modifications or improvements thereto.

U.S. Pat. No. 3,526,225 discloses an injector device for use in conjunction with an outside source of compressed air. The invention is therefore suitable only for use in a surgery (mass vaccinations). Moreover, it does not envisage the possibility of mixing ingredients.

U.S. Pat. No. 3,714,943 concerns a device able to accommodate within itself a plurality of special phials of which the contents can be injected one by one, but in this case too it is not possible to use the normal, commercially available phials and to load the medicament from the outside.

Moreover, the pressure needed to expel the medicament is generated with a gas compressed beforehand in a chamber within the device itself. This leads to problems of a gastight seal, as we said earlier.

U.S. Pat. No. 3,827,601 proposes a device using manual compression of a low power and is not relevant for the purposes of this invention.

U.S. Pat. No. 3,908,651 proposes an injector which enables the dose to be measured and the medicament to be loaded from the outside and to be drawn from normal, commercially available phials.

This apparatus has an injecting head with a complex structure and with a safety device that hinders the return of the medicament into the phial in the case of wrong usage.

Said device also comprises a very complicated fixture system and is suitable for administering the medicament from only one phial at a time, a fact which is a great drawback, as we said earlier. Moreover, the patent does not show how the injecting action is obtained, graduated and developed.

A further drawback lies in the fact that the device needs service keys when it has to be dismantled.

Our invention tends to overcome the drawbacks of the known art and provides many benefits and advantages.

Thus it is a purpose of the invention to provide an injector which makes possible a speedy and desired measured loading of the components to be injected during the filling stage.

It is also a purpose of the invention to enable two or more liquids to be loaded is measured quantities in sequence and to be mixed, also during the filling stage.

Another purpose of the invention is to provide an endermic injector device which can be used readily and at once and of which the need for maintenance can be substantially overlooked. A further purpose of the invention is to provide an injector of a relatively simple structure, easy to dismantle and to sterilize and provided with an outstanding degree of safety against wrong usage.

According to the invention it is possible to select aspiration from two or more commercially available phials suitably connected to the device, by pre-setting an appropriate valve.

In the case of two phials said valve has at least three positions, of which one allows the loaded liquid to be expelled, whereas the other two enable liquid to be aspirated from one or the other of said two phials, as desired, and the quantities to be measured from them in sequence.

According to the invention the injector device is equipped with dosage indicator means able to show the quantity of liquid aspirated from time to time during filling.

Filling takes place simply by means of negative pressure through the use of piston means drawn backwards with screw means, thereby overcoming the resistance of contrast spring means. Said spring means can be pre-loaded to the required value so as to supply the desired injection pressure and can be pre-loaded in steps or continuously.

Actuation of a trigger means makes possible the speedy disengagement of the piston, which is thrust quickly forward by the spring means into the chamber where there is the loaded fluid, with a resultant creation of the desired pressure in said frontal chamber holding said piston. Said pressure causes the discharge, through a nozzle, of the fluid held in said frontal chamber in the form of a jet under high pressure.

The invention is therefore embodied with an endermic injector device for making intracutaneous injections without a needle, said device being suitable for injecting under pressure at least one fluid drawn in measured doses from replaceable phials which are advantageously of a throwaway type, whereby means for aspirating fluid, means for expelling fluid, and names for producing the desired force of expulsion are included, said injector device comprising in cooperation:

an injector head having valve means for drawing and delivering fluid, a cylindrical chamber to contain fluid with a small removable piston, and safety means with an alignment head, a group to control aspiration and expulsion which comprises means for axial backward movement of said small piston, tripping means and spring means for axial movement of said small piston, means for regulating the pre-loading of said spring means and means for displaying the dose being loaded, and means to hold and position said phials.

We shall describe hereinafter, as a non-restrictive example, a preferred embodiment of the device of the invention.

The attached figures depict the following:

FIG. 1a shows a three-dimensional view of the device of the invention;

FIG. 1b shows a side view of the device of FIG. 1a;

Figure 2A:
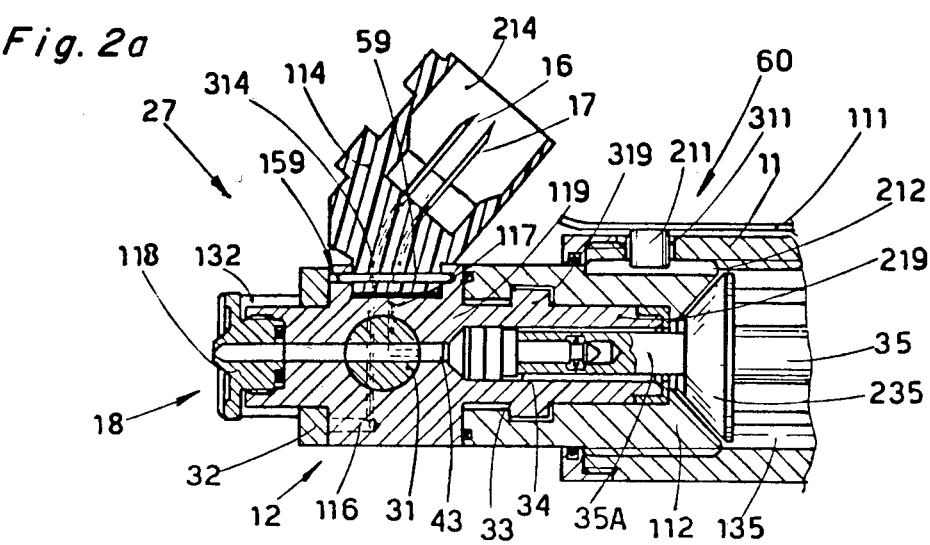
FIG. 2a shows a section of the zone of the chamber of the fluid and of the injector zone.

FIGS. 3a and 3b give two views, at right angles to each other, of the shutter of the valve;

FIG. 4a shows a section of the lodgement seating of the shutter of FIG. 3 in the body of the valve;

FIG. 4b shows the interacting working of the valve and of the alignment and safety head;

FIG. 5 shows the graduated crown with the flange;

FIG. 6 shows a preferred conformation of the small piston.

In the figures, 10 is the endermic injector of the invention. Outwardly the injector 10 consists substantially of a central body 11 of a substantially and advantageously cylindrical or prismatic shape, to which a head 12 and rear part 13 are connected.

The central body 11 can have ridges or milling so as to be easier to grip.

The head 12 comprises means 14 to fix and support phials 15 which can be perforated and of which in our example two can be inserted.

Said means 14 to fix phials consist, in this instance, of an connector 114 with two lodgements 214, one on each side; when two phials 15 are envisaged, there is one lodgement for each phial.

Each lodgement 214 has within it an aeration needle 16 and a needle 17 to draw liquid.

On the connector 114 means 57 are envisaged for fixture of a plug to protect the nozzle (not shown here) when the device is not in use.

Said means 57 fo fix a plug to protect the nozzle have the purpose of preventing said plug from being rested on outside surfaces with the danger of contamination by microbes.

Indeed, the invention envisages the ability to close with said plug the front part of the head 12 where the nozzle means 18 are located, thus isolating the head 12 from the environment.

For the same reason the invention likewise envisages the ability to plug the lodgements 214 with suitable plugs (not shown) when the device is not in use and phials 15 are not fitted to the connector 114.

The connector 114 is secured to the valve body 119 with at least locking pin means 59 inserted under pressure in our example.

The head 12 also comprises nozzle means 18 and valve means 19. The functions of said valve means 19 will be detailed in the description hereinafter.

The reciprocal axial positions of the head 12 and body 11 can be regulated advantageously so as to enable the working pressure to be regulated; said regulation can be obtained in ways which we shall describe hereinafter. The regulation can be envisaged as being obtained in steps or continuously.

The rear part 13 includes loading and tripping means 20 and means 21 for measuring or displaying the doses.

Outwardly the loading and tripping means 20 constitute a group to control aspiration and expulsion and comprise a rotatable cover 22, with a crank 23, from which a trigger, 24 protrudes so as to trip the device as soon as the latter has been filled.

The crank 23 is pivoted at 123 so that it can be folded back, as shown in FIG. 1a, when the device is not in use.

The measurement means 21 have on their outside a ring 25 which is preferably milled. Said ring 25 can be rotated and is towed periodically by the rotation of the rotatable cover 22 according to a ratio which is suitably pre-set.

The ring 25 bears a numbered scale 125 of which the indications can be seen through the window 126 in the immovable sleeve 26 solidly fixed to the body 11.

From a working point of view the device 10 can be deemed to consist of four sections (FIG. 2) or working groups cooperating closely with eech other:
  (a) an aspiration and ejection group 27 whither the fluid is aspirated and whence it is ejected at the required pressure;
  (b) a propulsion and pressure-regulation group 28 comprising the means that generate and regulate the pressure required;
  (c) loading group or group to control aspiration and expulsion 29, which comprises means to cock the means which generate the ejection pressure;
  (d) measurement group or means to display quantity of dose 30, which comprises the means able to make it possible to control the dose being loaded.

FIG. 2a shows a section of part of the body 11 and of the whole head 12, that is to say, it is possible to see both the aspiration and ejection group 27 and the part 60 regulating pressure in the group 28.

In the upper part of the head 12 there is the connector 114, of which it is possible to see one lodgement 214 with needles 16 and 17.

The needle 16 of each lodgement 214 gets air from a conduit 116 which communicates with the outside and which is opened and closed by the shutter 31 of the valve 19, which in our example can slide axially within the valve body 119.

According to the invention the shutter 31 will comprise advantageously circumferential sealing grooves 62. These grooves 62, which can be seen in FIGS. 3a and 3b, where they are drawn with thin lines, have a depth of about some hundredths of a millimeter and create a labyrinth seal, thus not requiring rubber packings, which deteriorate readily, on the shutter 31.

The needles 16 and 17 are shown as being separate elements but can also consist of only one element with the required number of channels. The needles 16–17 of each lodgement 214 are inserted with force into the respective channels 116–117 within the valve body 119 so as to ensure a hydraulic seal.

A packaging 314, which is made preferably of silicone rubber, is positioned between the valve body 119 and connector 114 and improves this seal by preventing any possible inflow of air or loss of fluid and therefore any danger of contamination.

The nozzle means 18 consist of a nozzle 118 which can be screwed onto the front of the valve body 119.

An alignment head means 32 (FIG. 4b) with fins 132 is able to slide axially on the valve body 119 and, by cooperating with the side notches in the shutter 31, serves to ensure the right positioning of said shutter 31 during ejection of the liquid (thus preventing wrong usage during the ejection, as will become clear hereinafter) and also to ensure the right positioning of the shutter 31 in its two end positions during filling of fluid.

An extension 219 which is located behind the valve body 119 accommodates a cylindrical chamber 33, wherein a small piston 34 which can move axially cooperates.

The small piston 34 is located at the end of a plunger 35, which in its turn can slide in a chamber 135.

This part of the head 12 forms the aspiration and ejection group 27.

All the rear part 219 of the valve body 119 is contained within a sleeve 112 fixed within the body 11.

The valve body 119 can be readily connected to and disconnected from said sleeve 112 by means of a bayonet fitting 319 located in the rear extension 219 and cooperating with a suitable seating in said sleeve 112.

Figure 2B:
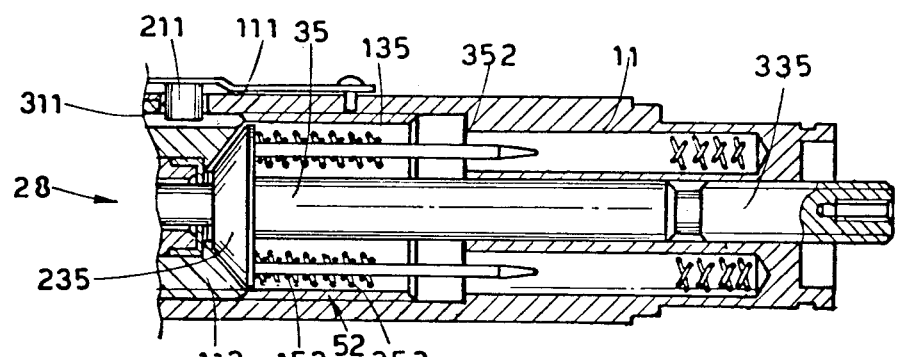
FIG. 2b shows a section of the zone of the contrast spring.
Figure 2C:
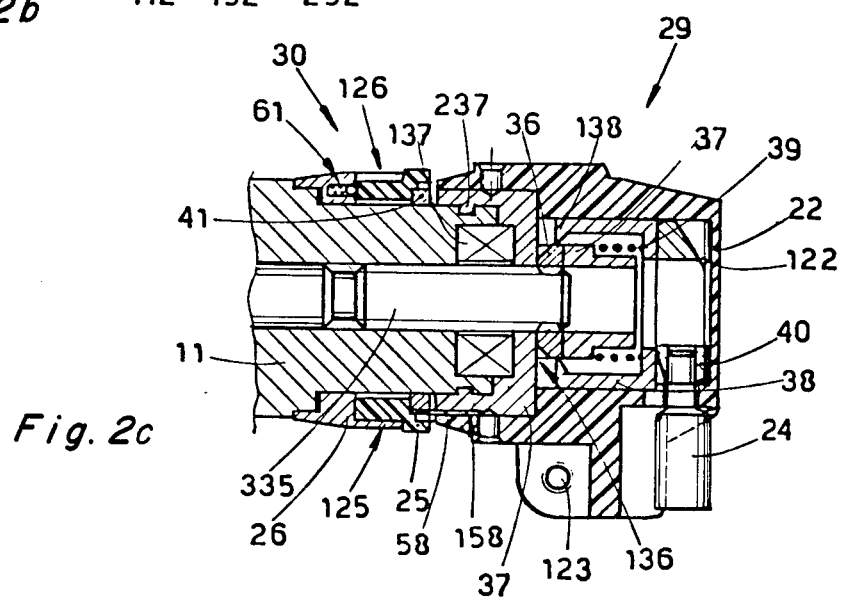
FIG. 2c shows a section of the loading and tripping zone.

FIG. 2b shows the propulsion and regulation group 28, which comprises the regulation sub-group 60.

In this figure the chamber 135 also lodges spring means 52, which may consist of one or more compression springs. In the example shown the spring means 52 comprise sets of springs 152 and 252 which are shown as being located one within the other.

The employment of a double set of spring means makes possible an ejecting characteristic consisting of initially very great pressure so as to overcome the resistance of the skin, said pressure lessening thereafter so as to provide a gradual injection of fluid.

Guide shafts 352 prevent sideways bending of the springs 152–252 during the cocking and loading phase and thus enable the axial thrust of said springs to be exploited to the utmost.

The use of springs 52 rather than a compressed gas eliminates not only the difficulties connected with the employment of seals between the various parts but also all problems arising from the employment of gas under pressure.

So as to permit the pressure to be regulated, it is possible to regulate the pre-loading of the springs by altering the axial position of the sleeve 112 which lodges the extension 119, and thus to use the group, or means, which regulates pre-loading or pressure 60.

In our example this axial positioning is obtained momentarily with a tongue 111 (FIG. 1a) bearing a prong 211 which is engaged, through a hole 311 in the body 11, in a hollow 212 made axially and peripherally in the sleeve 112.

When the elastic tongue 111 is raised, the prong 211 is disengaged from the hollow 212 and permits rotation of the sleeve 112, which can be thus rotated as desired by being screwed up or unscrewed.

After each full revolution or desired portion of a revolution the sleeve 112 is clamped again by the prong 211.

The system shown, which envisages one or more hollows 212, enables regulation to be carried out in steps. This group constitutes the means 60 for regulating the pre-loading of the spring means 52.

Reference means 56 consisting of notches or marks or any desired sign make it possible to check visually the axial position of the sleeve 112 in relation to the body 11 and thus the value of the pre-loading of the springs.

With the help of the loading group or group controlling aspiration and expulsion 29, the plunger 35 is made to go backwards and compresses the springs 52 by means of the collar 235 against which the springs 52 thrust and to which the guide shafts 352 are solidly fixed in our example.

Said backward movement of the plunger 35 is caused by the action of two or more comb-wise means 36, which consist of threaded half-rings or segments of rings on the threaded stub end 335.

Said comb-wise means 36 are lodged and radially guide within grooves on the sides of a sleeve 37, which is solidly fixed to the cover 22 and revolvably anchored to the body 11 by means of the bearing 137 and ridge 237 in our example.

In the lay-out shown said sleeve 37 is embodied with two counterpart halves so that it can be fitted to the body 11.

The annular circumferential ridge 237 cooperates with a suitable circumferential groove and thus hinders axial sliding of the sleeve 37 in relation to the body 11 itself but permits circumferential rotation of said sleeve 37.

A cup means 38 keeps the comb means 36 in position and conditions them. The spring 39 normally keeps the sleeve 37 and cup means 38 apart.

The actuation means 40, being actuated by the trigger 24 and resting on the pressure ring 122, thrusts the cup means 38 forwards and overcomes the elastic action of the spring 39.

The mutual cooperation of the forward end tooth 138 and the front bevel 136 of the comb means 36 creates the required conditioning.

Displacing the cup means 38 forwards, the tooth 138 begins to cooperate with the bevel 136; the comb means 36 are freed thereby and can move backwards in a radial direction within the cup means 38 owing to the inner diameter of the cup means 38 being greater than that of the end portion 138 thereof, and thus become disengaged from the screw threads of the stub end 335.

The stub end 335, being thus disengaged from the comb means 36 and freed from said conditioning, is thrust forwards by the springs 52 acting on the collar 235.

The measurement group 30 comprises an immovable cam 41 (FIG. 5) coaxial with the ring 25 and secured to the central body 11.

A steel wire 58, drawn by the sleeve 37, runs between the cam 41 and ring 25. Said wire 58 is lodged partly in the sleeve 37 within a peripheral lengthwise seating 158 and is solidly fixed circumferentially to the sleeve 37 itself.

When the wire 58 meets a ridge 141, it moves radially outwards in our example and engages a notch 225, thus pulling the ring 25 through a number of clicks determined by the circumferential peripheral extent of the ridge 141.

The notches 225 run near the ridges 141, so that, as the wire 58 runs on the cam 41, it has to act on the relative notch when the ridge 141 rises again.

At every revolution of the sleeve 37 solidly fixed to the cover 22, therefore, the ring 25 carries out a number of clicks determined by the number of the ridges 141 and also carries out, for each click, a forward movement determined by the circumferential extent of the ridge 141.

The clicks are fixed momentarily by notch means 61 or hollows made in the ring 25 and cooperating with spring means (tongue-wise, spring with ball, etc.) located in the sleeve 26.

The number of clicks can be read on the numbered scale 125 through the window 126 (FIG. 1b) and in this way the quantity of the dose loaded can be determined.

FIGS. 3 and 4 respectively show the shutter 31 and valve body 119.

The valve 19 works as follows: the shutter 31 (FIG. 4) can be moved sideways to one side or the other to select the phial from which it is wished to draw the liquid. In this way one or the other of two filling holes 42 is placed so as to coincide with the relative channel 117 of the valve 19.

The sideways path of the shutter 31 and its circumferential position are conditioned by the cooperation of the fins 132 of the head 32 in the fully forward position 32A (see FIG. 4b) together with the side notches 45.

The form of the holes 42 (see FIG. 4) is such that in each of the two sideways positions of the shutter 31 said holes 42 put the relative filling channel 117 into communication with that tract of the central channel 43 of the valve body 119 which is oriented towards the chamber 33 with which it communicates.

Likewise the aeration holes 44 are made to coincide with the aeration channels 116, which are thus open and communicate with the outside after the fitting of suitable filter means.

When the shutter 31 is in its middle position, the holes 42–44 no longer coincide with the respective channels 117–116, which are therefore closed.

The middle position of the shutter 31 is obtained automatically by means of fins 132 owing to the backward movement of the head 32 when the latter is thrust against the skin of the patient. Indeed, the fins 132 act on the side notches 45 and align the shutter 31 in the middle position.

The shutter 31 can take up, as wished, the partly axially displaced two side positions (FIG. 4b—see the line of dashes 31A) while the head 32 is in the fully outward position 32A. In this case the fins 132 delimit sideways axial deviation, and the shutter 31 puts the holes 42–44 in positions 42A and 44A so that said holes 42–44 are ready for the operations of charging fluid from the phials 15 and of sending air into said phials 15.

In the middle position the central orifice 46 coincides with the central channel 43 and puts the chamber 33 into communication with the nozzle 18. In this way the liquid which has been aspirated beforehand can then be ejected through said channel 43.

FIG. 6 shows a detail of the small piston 34. A stub 134 with an elastic ring 234 is inserted within the head 35A of the plunger 35.

The elastic ring 234 is engaged in an appropriate circumferential seating 53 located in the head 35A and permits ready attachment and removal of the small piston 34, which in this way can be speedily replaced.

During aspiration this lay-out prevents the small piston 34 from becoming detached from the plunger 35 since the force required for this would be greater than the force applied by the negative pressure developing in the chamber 33.

The head 334 of the small piston 34 of our example comprises a brass ring 47, an O-ring 48 with outer ring 49 and a frontal ring 50 connected to the pin 51 by caulking 151.

In the lay-out shown the small piston 34 can be replaced if it becomes worn.

When the injector device 10 is being filled, the plunger 35 goes backwards initially without drawing the small piston 34, until the bevelled surface 153 of the seating 53 engages the ring 234.

After this initial travel without filling, the small piston 34 goes backwards together with the plunger 35 and aspirates liquid into the chamber 33.

Account of said travel without filling is taken by envisaging an appropriate corresponding dead space at the beginning of the numbered scale on the ring 25.

During ejection the forward surface 54 of the plunger 35 acts against the collar 55 of the small piston 34, which bears the thrust.

The device of the invention works in the following way:

(a) One or more phials 15 are inserted into the connector 114. The head 32 is brought to the forward position 32A (FIG. 1b).

(b) The shutter 31 is displaced sideways so as to select the phial 15 desired. The course of the shutter 31 and its circumferential position are conditioned by the fins 132 cooperating with the notches 45. In this way the aeration channel 116 and filling channel 117 respectively corresponding to the selected phial 15 are opened.

(c) The rotatable cover 22, which draws the sleeve 37 with the combs 36 engaged in the threaded tract 335 of the plunger 35 is rotated by means of the crank 23. By rotating, said combs 36 make the stub end 335 go backwards and therewith the plunger 35, which pulls back the small piston 34, thus creating the required negative pressure in the chamber 33. The chamber 33 is thus filled with liquid to the value desired since it is possible to read the quantity of liquid aspirated through the window 126.

(d) Any aspiration of the second fluid from the other phial 15 is now carried out and the two liquids are thus mixed in the chamber 33, which has been left free owing to the backward movement of the small piston 34. The shutter 31 is switched to the other phial and the procedure goes on as in (b) and (c). The sum of the quantities of liquid aspirated from the first and second phials 15 is read in a window 126.

(e) The end 12 of the device 10 is pressed agains the patients skin so that the head 32 moves back and the oblique fins 132 align the shutter 31 in the valve body 119, thereby closing the channels 116 and 117 and opening the central channel 43 in line with the central orifice 46.

(f) Actuation of the trigger 24 displaces axially the cup means 38, which causes radial movement of the comb means 36 within the cup means 38 itself, thus preventing the further displacement of said comb means 36. The stub end 335 is therefore disengaged therefrom and the plunger 35, being thrust by the springs, pushes the small piston 34 back into the chamber 33. The liquid is ejected thereby at the desired pressure through the central channel 43 and nozzle 118.

We have described herein a preferred embodiment of the invention, but many variants are possible. The shapes and sizes of the parts can be changed and the phials 15 can be more than two in number and be positioned differently.

It is also possible to use varied kinds of spring means, perhaps having a progressive action. It is also possible to arrange for a shutter 31 which rotates instead of sliding axially within the valve body 19.

These and other variants are all possible for a person skilled in this field without departing thereby from the scope of the idea of the solution of the invention.

INDEX

10—injector
11—central body
111—tongue
211—prong
311—hole
12—end
112—sleeve
212—hollow
13—rear part
14—means to fix phials or means to hold and position phials
114—connector
214—lodgements
314—packing
15—phials which can be perforated
16—aeration needle
116—aeration channel
17—needle to draw liquid
117—filling channel
18—nozzle means
118—nozzle which can be screwed
19—valve means
119—valve body
219—rear extension
319—bayonet fitting
20—loading and tripping means—means to control aspiration and expulsion
21—means for measuring or displaying the doses
22—rotatable cover
122—pressure ring
23—crank
123—pivot
24—trigger
25—ring
125—numbered scale
225—notches
26—immovable sleeve
126—window
27—aspiration and ejection group
28—propulsion group
29—loading group or means to control aspiration and expulsion
30—measurement group or means to display quantity of dose
31—shutter
31A—side position of shutter
32—alignment head
32A—forward position of head
132—fins
33—cylindrical chamber
34—small piston
134—stub
234—elastic ring
334—head of small piston 35—plunger
35A—head of plunger
135—chamber
235—collar
335—threaded stub end
36—threaded comb-wise means
136—front bevel
37—sleeve
137—bearing
237—ridge
38—cup means
138—forward end tooth
39—spring
40—actuation means
41—cam
141—ridges
42—filling holes
42A—working position of filling holes
43—central channel
44—aeration holes
44A—working position of aeration holes
45—side notches
46—central orifice
47—brass ring
48—O-ring
49—outer ring
50—frontal ring
51—pin
151—caulking
52—spring means
152—inner spring
252—outer spring
352—guide shafts
53—circumferential seating
153—bevelled surfaces
54—forward surface of plunger
55—collar of small piston
56—reference means
57—means to fix plugs
58—steel wire
158—seating for wire
59—locking pin
159—hole
60—means to regulate pre-loading or pressure
61—notch means
62—sealing grooves.

We claim:

1. An endermic injector device for subcutaneous injections without a needle, said device being suitable for injecting under pressure at least one fluid drawn in a measured dose from replaceable phials, preferably of a throwaway type, said device comprising
nozzle means,
means to aspirate fluid,
means to expel fluid, and
means to provide the required force of expulsion, said device further comprising in cooperation
means for aspiration and injection comprising (1) a valve means to draw and deliver fluid, (2) a cylindrical chamber for containing fluid together with a removable small piston, and (3) safety means having an alignment head,
means to control aspiration and expulsion comprising (1) means for axial withdrawal of said small piston, (2) tripping means, and (3) spring means for the forward axial movement of said small piston,
means to display the quantity of said fluid, and
means to hold and position said phials comprising at least one containing lodgement with two needles cooperating with valve means for temporary connection with said cylindrical chamber and with the atmosphere respectively.

2. The endermic injector device of claim 1 wherein said valve means comprise shutter means able to take up an injecting position and a specific filling position for each lodgement holding said phials.

3. The endermic injector device of claim 2 wherein the injecting position of said shutter means of the valve means is conditioned by safety means with an alignment head in the backward position.

4. The endermic injector device of claim 1 wherein the extreme loading positions of said shutter means of the valve means are defined by fin means on alignment head means in a position forward of the fin means.

5. The endermic injector device of claim 2 wherein said cylindrical chamber means communicates respectively with said phials and with the nozzle means by the momentary reciprocal position of said shutter means in the valve means.

6. The endermic injector device of claim 1 wherein the means for axial withdrawal of said small piston comprise in cooperation;
radially movable comb means,
sleeve means to position radially and to guide said comb means,
cup means having a forward end tooth cooperating with the back and with the forward bevelling of said comb means in the momentary radial positioning of said comb means in relation to threaded stub means,
threaded stub means solidly fixed to plunger means that bear at their end said small piston in such a way that said small piston can be removed,
spring means for the normal positioning of said cup means, and
actuation means to vary momentarily the reciprocal position of said cup means in relation to said comb means, said actuation means being actuated by trigger means.

7. The endermic injector device of claim 6 wherein said plunger means comprise, at a desired intermediate position, collar means to position and resist spring displacement means together with guide shaft means.

8. The endermic injector device of claim 1 wherein the means for axial withdrawal of said small piston govern the means that display the quantity of the dose.

9. The endermic injector device of claim 1 wherein the means that display the quantity of said fluid comprise in cooperation:
cam means with ridge means, and
ring means with notches facing said ridge means and cooperating therewith, said ring means comprising numbered scale means, whereby said ring means are periodically advanced (tripped) temporarily by steel wire means solidly fixed to the withdrawal means and acting between said cam means and said notches.

10. The endermic injector device of claim 6 wherein said means to regulate the pre-loading of said spring means are obtained by means of the reciprocal axial adjustable position of said sleeve means in relation to the central body, whereby there are advantageously visible reference means and disconnectable means for temporary fixture of the determined reciprocal axial position.

11. The endermic injector device of claim 1 wherein the injecting end of the device can be disconnected from said sleeve means for sterilization, such temporary connection being obtained advantageously with bayonet fitting means.

12. The endermic injector device of claim 1 wherein said small piston comprises momentary anchorage means having an elastic ring cooperating with circumferential seating means located in said plunger means.

13. The endermic injector device of claim 12 wherein the initial relative play in aspiration as between the elastic ring means and circumferential seating means is shown visually on the ring means.

14. An endermic injector device for subcutaneous injections without a needle, said device being suitable for injecting under pressure at least one fluid drawn in a measured dose from replaceable phials, preferably of a throwaway type, said device comprising
    nozzle means,
    means to aspirate fluid,
    means to expel fluid, and
    means to provide the required force of expulsion, said device further comprising in cooperation
    means for aspiration and injection comprising (1) a valve means to draw and deliver fluid, (2) a cylindrical chamber for containing said fluid together with a removable small piston and (3) safety means having an axially movable alignment head,
    means to control aspiration and expulsion comprising (1) means to axial withdrawal of said small piston, (2) tripping means, and (3) spring means for the forward axial movement of said small piston,
    means to display the quantity of said fluid, and
    means to hold and position said phials.

* * * * *